US011807603B2

(12) United States Patent
Von Hof et al.

(10) Patent No.: US 11,807,603 B2
(45) Date of Patent: Nov. 7, 2023

(54) CROSS-LINKED POLYGLYCEROL ESTERS

(71) Applicant: Evonik Operations GmbH, Essen (DE)

(72) Inventors: Jan Marian Von Hof, Bochum (DE); Achim Friedrich, Hattingen (DE); Wolfgang Berkels, Bottrop (DE); Barbara Hohenberg, Gelsenkirchen (DE); Oliver Springer, Wesel (DE); Juergen Meyer, Essen (DE)

(73) Assignee: Evonik Operations GmbH, Essen (DE)

( * ) Notice: Subject to any disclaimer, the term of this patent is extended or adjusted under 35 U.S.C. 154(b) by 324 days.

(21) Appl. No.: 16/322,566

(22) PCT Filed: May 15, 2017

(86) PCT No.: PCT/EP2017/061563
§ 371 (c)(1),
(2) Date: Feb. 1, 2019

(87) PCT Pub. No.: WO2018/033259
PCT Pub. Date: Feb. 22, 2018

(65) Prior Publication Data
US 2019/0202771 A1 Jul. 4, 2019

(30) Foreign Application Priority Data
Aug. 18, 2016 (EP) ..................... 16184676

(51) Int. Cl.
C07C 69/675 (2006.01)
C07C 67/08 (2006.01)
A61K 47/14 (2017.01)
A61K 8/06 (2006.01)
A61Q 19/00 (2006.01)
A61K 8/39 (2006.01)
C09K 23/00 (2022.01)
A61K 8/37 (2006.01)
A61Q 1/02 (2006.01)
A61Q 15/00 (2006.01)
A61Q 17/04 (2006.01)

(52) U.S. Cl.
CPC ............ *C07C 69/675* (2013.01); *A61K 8/064* (2013.01); *A61K 8/375* (2013.01); *A61K 8/39* (2013.01); *A61K 47/14* (2013.01); *A61Q 1/02* (2013.01); *A61Q 15/00* (2013.01); *A61Q 17/04* (2013.01); *A61Q 19/00* (2013.01); *A61Q 19/007* (2013.01); *C07C 67/08* (2013.01); *C09K 23/00* (2022.01); *A61K 2800/10* (2013.01)

(58) Field of Classification Search
CPC ....... C07C 69/675; C07C 67/08; A61K 8/375; A61K 47/14
See application file for complete search history.

(56) References Cited

U.S. PATENT DOCUMENTS

| 3,256,304 | A | * | 6/1966 | Fischer | ................. C07C 51/487 560/127 |
|---|---|---|---|---|---|
| 6,242,499 | B1 | | 6/2001 | Gruning et al. | |
| 6,581,613 | B2 | | 6/2003 | Berkels et al. | |
| 7,851,511 | B2 | | 12/2010 | Allef et al. | |
| 7,906,664 | B2 | * | 3/2011 | Allef | ..................... C08G 63/66 554/166 |
| 7,910,119 | B2 | | 3/2011 | Allef et al. | |
| 8,211,792 | B2 | | 7/2012 | Meyer et al. | |
| 8,642,525 | B2 | | 2/2014 | Herrwerth et al. | |
| 8,653,289 | B2 | | 2/2014 | Wenk et al. | |
| 8,795,692 | B2 | | 8/2014 | Hameyer et al. | |
| 8,993,792 | B2 | | 3/2015 | Hartung et al. | |
| 9,409,853 | B2 | | 8/2016 | Schuch et al. | |
| 9,427,385 | B2 | | 8/2016 | Meyer et al. | |
| 9,616,007 | B2 | | 4/2017 | Herrwerth et al. | |
| 9,738,797 | B2 | | 8/2017 | Nilewski et al. | |
| 9,776,951 | B2 | | 10/2017 | Friedrich et al. | |
| 9,890,107 | B2 | | 2/2018 | Schuch et al. | |
| 2006/0165627 | A1 | * | 7/2006 | Allef | ..................... C08G 63/60 424/70.11 |
| 2007/0092470 | A1 | | 4/2007 | Allef et al. | |
| 2008/0004357 | A1 | | 1/2008 | Meyer et al. | |
| 2008/0108709 | A1 | | 5/2008 | Meyer et al. | |
| 2010/0310617 | A1 | * | 12/2010 | Zhang | .................... A61K 8/064 424/401 |
| 2013/0071340 | A1 | | 3/2013 | Wenk et al. | |
| 2014/0039071 | A1 | | 2/2014 | Thum et al. | |
| 2016/0165627 | A1 | | 6/2016 | Uemura et al. | |
| 2017/0202770 | A1 | | 7/2017 | Friedrich et al. | |

(Continued)

FOREIGN PATENT DOCUMENTS

| EP | 0835862 | A1 | 4/1998 |
|---|---|---|---|
| EP | 1500427 | A2 | 1/2005 |

(Continued)

OTHER PUBLICATIONS

German language Written Opinion dated Aug. 18, 2017 in PCT/EP2017/061563 (5 pages).

(Continued)

*Primary Examiner* — Matthew P Coughlin
(74) *Attorney, Agent, or Firm* — Grüneberg and Myers PLLC

(57) ABSTRACT

The invention relates to a polyglycerol partial ester obtainable by esterification of a polyglycerol with a carboxylic acid mixture comprising at least one polyhydroxycarboxylic acid of a hydroxycarboxylic acid having 8 to 32 carbon atoms, at least one short-chain dicarboxylic acid having 2 to 16, preferably 6 to 14, particularly preferably 8 to 12, carbon atoms, at least one long-chain dicarboxylic acid having 24 to 44, preferably 30 to 40, particularly preferably 34 to 38, carbon atoms, and at least one fatty acid selected from linear, unsaturated and branched, saturated fatty acids having 14 to 24 carbon atoms, to a method for preparing polyglycerol partial esters, and to the use of corresponding polyglycerol partial esters as W/O emulsifier.

20 Claims, No Drawings

(56) References Cited

U.S. PATENT DOCUMENTS

2018/0036218 A1    2/2018  Gu et al.
2018/0216023 A1    8/2018  Maier et al.
2018/0344602 A1   12/2018  Schuch et al.

FOREIGN PATENT DOCUMENTS

EP        1683781  A2    7/2006
EP        2319484  A2    5/2011
WO     2014090615  A2    6/2014

OTHER PUBLICATIONS

International Search Report dated Aug. 18, 2017 in PCT/EP2017/061563 (2 pages).
Liebig et al., U.S. Appl. No. 16/312,480, filed Dec. 21, 2018.

* cited by examiner

CROSS-LINKED POLYGLYCEROL ESTERS

CROSS REFERENCE TO RELATED APPLICATIONS

This application is a 35 U.S.C. § 371 U.S. national phase entry of International Application No. PCT/EP2017/061563 having an international filing date of May 15, 2017, which claims the benefit of European Application No. 16184676.1 filed Aug. 18, 2016.

FIELD

The invention relates to a polyglycerol partial ester obtainable by esterification of a polyglycerol with a carboxylic acid mixture comprising at least one polyhydroxycarboxylic acid of a hydroxycarboxylic acid having 8 to 32 carbon atoms, at least one short-chain dicarboxylic acid having 2 to 16, preferably 6 to 14, particularly preferably 8 to 12, carbon atoms, at least one long-chain dicarboxylic acid having 24 to 44, preferably 30 to 40, particularly preferably 34 to 38, carbon atoms, and at least one fatty acid selected from linear, unsaturated and branched, saturated fatty acids having 14 to 24 carbon atoms, to a method for preparing polyglycerol partial esters, and to the use of corresponding polyglycerol partial esters as W/O emulsifier.

BACKGROUND

EP0835862 describes polyglycerol partial esters of saturated or unsaturated, linear or branched fatty acids and polyfunctional carboxylic acids, obtainable by esterification of a polyglycerol mixture with saturated or unsaturated, linear or branched fatty acids having 12 to 22 carbon atoms and polyfunctional carboxylic acids having 4 to 54 carbon atoms and an average functionality of 2 to 2.4, wherein the degree of esterification of the polyglycerol mixture is from to 75%. The polyglycerol preferably has an average degree of condensation n of ≥2, preferably 3 to 4. The polyfunctional carboxylic acids preferably used are long-chain dimer acids obtained by catalysed dimerization of unsaturated fatty acids having 12 to 22 carbon atoms. Polyhydroxy fatty acids are not used.

EP1683781 describes polyglycerol partial esters of polyricinoleic acid and polyfunctional carboxylic acids, obtainable by esterification a) of a polyglycerol mixture with b) at least one particular polyricinoleic acid and optionally b1) polyhydroxystearic acid and c) at least one di- and/or tricarboxylic acid and d) at least one fatty acid according to methods known per se. The polyglycerol preferably has an average degree of condensation n of 1 to 11, preferably 2 to 6. The di- and/or tricarboxylic acids preferably used are short-chain ones, and the additional fatty acid components preferably used are saturated fatty acids. In the examples, sebacic acid and polyricinoleic acid is always reacted with polyglycerol.

EP1500427 describes polyglycerol partial esters of polyhydroxystearic acid and polyfunctional carboxylic acids, obtainable by esterification of a polyglycerol mixture with polyhydroxystearic acid and di- and/or tricarboxylic acids and optionally/or with dimeric fatty acids and fatty acids having 6 to 22 carbon atoms. The polyglycerol preferably has an average degree of condensation n of 1 to 11, preferably 2 to 6, particularly preferably 3 to 6. The di- and/or tricarboxylic acids preferably used are alkanedicarboxylic acids having 4 to 14 carbon atoms. The document teaches that the use of relatively short-chain (C4 to C14) di- or tricarboxylic acids instead of long-chain (>C24) dimer acids is preferred for the intended use as emulsifier.

A disadvantage of the polyglycerol partial esters described in the prior art is that these are not able to stabilize especially high amounts of natural oils in W/O emulsions. In addition, it is not possible, solely with the PEG-free polyglycerol partial esters described in the prior art, thus for example with those of EP1683781, EP1500427 or EP0835862, to stabilize so-called quick-breaking emulsions, as described in WO2014090615 or EP2319484 for example.

The problem addressed by the invention was that of developing polyglycerol partial esters having a capacity for emulsion stabilization that is improved compared to the prior art, especially in the case of a high amount of oil.

SUMMARY

Surprisingly, it has been found that the polyglycerol partial esters described below are able to solve the problem addressed by the invention.

The present invention therefore provides a polyglycerol partial ester obtainable by esterification of a polyglycerol with a carboxylic acid mixture comprising:
  a) at least one polyhydroxycarboxylic acid of a hydroxycarboxylic acid having 8 to 32, preferably 12 to 22, particularly preferably 14 to 18, carbon atoms,
  b) at least one short-chain dicarboxylic acid having 2 to 16, preferably 6 to 14, particularly preferably 8 to 12, carbon atoms,
  c) at least one long-chain dicarboxylic acid having 24 to 44, preferably 30 to 40, particularly preferably 34 to 38, carbon atoms, and
  d) at least one fatty acid selected from linear, unsaturated and branched, saturated fatty acids having 14 to 24, preferably 16 to 20, carbon atoms.

The invention further provides a method for preparing such polyglycerol partial esters, and for the use of corresponding polyglycerol partial esters as W/O emulsifier.

The advantages are:

An advantage of the present invention is that it is possible with the polyglycerol partial esters to formulate excellent quick-breaking systems which, as W/O emulsions, have extremely large amounts of internal water phase, especially at an extremely low emulsifier concentration, and release the internal phase when distributed on the skin. With the emulsifiers according to the invention, such quick-breaking systems can for the first time also be prepared completely based on natural ingredients.

A further advantage of the present invention is that high proportions of natural oils such as, for example, almond oil in emulsions are well stabilized too.

A further advantage of the present invention is that emulsions can be stabilized over a broad viscosity range from sprays to lotions and up to creams.

A further advantage of the present invention is that emulsions based on emulsifiers according to the invention have a very good compatibility with propellants, such as, for example, mixtures of propane, n-butane and iso-butane, and thus simplify the production of aerosol systems. Another advantage of the present invention is that the emulsions stabilized with the described polyglycerol partial esters can be formulated PEG-free.

A further advantage of the present invention is that the skin feel of the emulsions stabilized with the described polyglycerol partial esters is at least just as good as with the emulsifiers of the prior art.

Another advantage of the present invention is that the oil fraction of the emulsions stabilized with the described polyglycerol partial esters is rapidly absorbed through the skin.

A further advantage of the present invention is that emulsions based on the emulsifiers according to the invention have a very high electrolyte tolerance, for example are emulsion-stable with respect to 7% by weight of NaCl.

The polyglycerol partial esters according to the invention are mixtures of different substances; it will therefore be clear to the person skilled in the art that specified numeric values may be average values over the mixture.

In the context of the present invention, the term "polyglycerol" is to be understood as meaning a polyglycerol which may also comprise glycerol. Consequently, for the purposes of calculating amounts, masses and the like, any glycerol fraction should also be taken into consideration. In the context of the present invention, polyglycerols are therefore also mixtures comprising at least one glycerol oligomer and glycerol. Glycerol oligomers are to be understood in each case as meaning all relevant structures, i.e., for example, linear, branched and cyclic compounds. The same applies to the term "polyglycerol partial ester" in connection with the present invention.

Unless stated otherwise, all percentages (%) given are percentages by mass.

A polyglycerol partial ester preferred according to the invention is characterized in that the polyglycerol used has an average degree of condensation of 1.5 to 15, preferably of 2 to 6, particularly preferably of 3 to 5.

The average degree of polymerization N of the polyglycerol is calculated via its hydroxyl number (OHN, in mg KOH/g) according to the following formula:

$$N = \frac{(112200 - 18 \cdot OHN)}{(74 \cdot OHN - 56100)}$$

Suitable methods for determining the hydroxyl number are particularly those according to DGF C-V 17 a (53), Ph. Eur. 2.5.3 Method A and DIN 53240.

A polyglycerol partial ester preferred according to the invention is therefore characterized in that the polyglycerol used has a hydroxyl number of 1520 to 845, preferably of 1350 to 970, particularly preferably of 1170 to 1010 mg KOH/g.

The polyglycerol used can be provided by different conventional methods such as, for example, polymerization of glycidol (e.g. base-catalysed), polymerization of epichlorohydrin (for example in the presence of equimolar amounts of a base such as NaOH) or polycondensation of glycerol. According to the invention, preference is given to the provision of the polyglycerol by the condensation of glycerol, in particular in the presence of catalytic amounts of a base, in particular NaOH or KOH. Suitable reaction conditions are temperatures between 200 and 260° C. and reduced pressure in a range between 20 and 800 mbar, in particular between 50 and 500 mbar, as a result of which facilitated water removal is possible. Corresponding methods can be found in standard chemistry textbooks such as, for example, Rompp.

According to the invention, it is preferred that the polyglycerol used comprises
0 to 15% glycerol,
to 40% diglycerol,
10 to 50% triglycerol,
5 to 25% tetraglycerol and
0 to 55% pentaglycerol and higher glycerols.

To determine the oligomer distribution by means of GC, an aliquot of the polyglycerol is dissolved in 2 ml of pyridine:chloroform (4:1). 0.5 ml of this solution is admixed with 1 ml of MSTFA [N-methyl-N-(trimethylsilyl)trifluoroacetamide]. The alcohols are quantitatively converted to their trimethylsilyl ethers by reaction at 80° C. (30 minutes) and then analysed by means of GC/FID.

This is carried out in a gas chromatograph equipped with a split/splitless injector, a capillary column and a flame ionization detector, under the following conditions:
Injector: 290° C., split 30 ml
Injection volume: 1 µl
Column: 30 m*0.32 mm HP1 0.25 µm
Carrier gas: Helium, constant flow, 2 ml/min
Temperature program: 80° C.-300° C. at 4° C./min, then conditioning for 10 minutes at 300° C.
Detector: FID at 310° C.
Hydrogen 35 ml/min
Air 240 ml/min
Make-up gas 12 ml/min Glycerol, diglycerol, triglycerol and tetraglycerol are separated and their mass fraction is determined by an internal standard method. For this, the GC system is calibrated by analysing mixtures of the glycerols to be investigated and of the internal standard with known composition, with triglycerol and tetraglycerol being evaluated as diglycerol. Pentaglycerol and higher glycerols can be determined by subtraction of the glycerol, diglycerol, triglycerol and tetraglycerol proportions from 100%.

The polyglycerol partial ester according to the invention is obtainable by esterification of a polyglycerol with a carboxylic acid mixture comprising components a), b), c) and d). It is preferred in accordance with the invention if components a), b), c) and d) make up in total at least 80% by weight, preferably at least 90% by weight, particularly preferably at least 95% by weight, based on the total carboxylic acid mixture used.

A polyglycerol partial ester preferred according to the invention is characterized in that the polyhydroxycarboxylic acid is selected from polyhydroxystearic acid and polyricinoleic acid, particular preference being given to polyhydroxystearic acid.

A polyglycerol partial ester preferred according to the invention is characterized in that the polyhydroxycarboxylic acid has an average degree of condensation of 1.5 to 9, preferably of 2 to 7, particularly preferably of 3 to 5.

The average degree of condensation of the polyhydroxycarboxylic acid can be determined as follows:

$$N = \frac{\frac{56106}{AN} - 18.02}{M_{Monomer} - 18.02}$$

where N = average degree of condensation of the polyhydroxycarboxylic acid
AN = acid number [mg KOH/g]
$M_{Monomer}$ = molecular weight of the monomer [g/mol], e.g. 300.48 g/mol for hydroxystearic acid Suitable methods for determining the acid number are particularly those according to DGF C-V 2, DIN EN ISO 2114, Ph. Eur. 2.5.1, ISO 3682 and ASTM D 974.

Suitable methods for determining the iodine number are particularly those according to DGF C-V 11 a (53) and Ph. Eur. 2.5.4 (method A).

The polyhydroxycarboxylic acids used according to the invention are, for example, prepared by polycondensation of at least one appropriate hydroxycarboxylic acid. Suitable reaction conditions are temperatures between 180 and 260° C. and atmospheric pressure or else reduced pressure in a range between 20 and 800 mbar, in particular between 50 and 500 mbar. Preferably, use is made here of hydroxystearic acid, especially 12-hydroxystearic acid, which is obtained by hardening of ricinoleic acid or technical-grade castor oil fatty acid. What is obtained and preferably used here are polyhydroxystearic acids which, by preference, have acid numbers between 188 and 20, preferably between 97 and 33, particularly preferably between 65 and 40.

It is preferred in accordance with the invention if the short-chain dicarboxylic acid in the polyglycerol partial ester according to the invention is selected from aliphatic, linear dicarboxylic acids, in particular oxalic acid, malonic acid, succinic acid, glutaric acid, adipic acid, pimelic acid, suberic acid, azelaic acid, sebacic acid, dodecanedioic acid, wherein sebacic acid is particularly preferred.

A polyglycerol partial ester preferred according to the invention is characterized in that the long-chain dicarboxylic acid is selected from those obtainable from the dimerization of oleic acid and/or linoleic acid. The mixtures obtainable from such a process known as dimer fatty acids can comprise not only the long-chain acyclic and cyclic dicarboxylic acids but also, to a minor extent, polymeric fatty acids (trimeric and higher functional), which in turn contribute to the proportion of the carboxylic acid mixture used which is not encompassed by components a) to d). The functionality of the mixture obtainable from the dimerization of oleic acid and/or linoleic acid should preferably not exceed, on molar average, a value of 2.4. For the preparation and use of dimer fatty acids and the physical and chemical properties thereof, reference is also made to the publication "*The Dimer Acids: The chemical and physical properties, reactions and applications*", Ed. E. C. Leonard; Humko Sheffield Chemical, 1975, Memphis, Tenn.

It is preferred in accordance with the invention if the at least one fatty acid selected from linear, unsaturated and branched, saturated fatty acid in the polyglycerol partial ester according to the invention is selected from isostearic acid, undecylenic acid, myristoleic acid, palmitoleic acid, petroselinic acid, oleic acid, elaidic acid, vaccenic acid, gadoleic acid, icosenoic acid, cetoleic acid, erucic acid, nervonic acid, linoleic acid, alpha-linolenic acid, gamma-linolenic acid, calendulic acid, punicic acid, alpha-elaeostearic acid, beta-elaeostearic acid, arachidonic acid, timnodonic acid, clupanodonic acid, cervonic acid, wherein oleic acid and isostearic acid are particularly preferred.

A polyglycerol partial ester preferred according to the invention is characterized in that the degree of esterification is from 35 to 95%, preferably from 40 to 90%, particularly preferably from 45 to 85%, of all OH groups present in the polyglycerol partial ester, including the ones present in the polyhydroxycarboxylic acid.

The degree of esterification of all OH groups can be determined according to the following formula via the hydroxyl number, the acid number and the hydrolysis number:

$$\text{Degree of esterification} = \frac{HN - AN}{HN - AN + OHN} \cdot 100$$

where
HN = hydrolysis number
AN = acid number
OHN = hydroxyl number

Suitable methods for determining the hydrolysis number are particularly those according to DGF C-V 3, DIN EN ISO 3681 and Ph. Eur. 2.5.6.

A polyglycerol partial ester preferred according to the invention is characterized in that, in the esterification, 0.1 to 2, preferably 0.3 to 1, particularly preferably 0.4 to 0.8, mol of component a),
0.1 to 2, preferably 0.2 to 0.9, particularly preferably 0.3 to 0.6, mol of component b),
0.1 to 2, preferably 0.2 to 0.9, particularly preferably 0.2 to 0.5, mol of component c), and
0.5 to 4, preferably 0.8 to 3, particularly preferably 1.2 to 2.2, mol of component d)
are used per mole of polyglycerol.

A polyglycerol partial ester preferred according to the invention is characterized in that, in the esterification, the molar ratio of b) to c) is from 0.2:1.0 to 1.0:0.2, preferably
from 0.5:1.0 to 1.0:0.5, more preferably
from 0.7:1.0 to 1.0:0.7.

The polyglycerol partial esters of the present invention can be prepared by classical esterification methods, as described in EP0835862, EP1683781 and EP1500427 for example. Preferably, the polyglycerol partial esters of the present invention are prepared using the method according to the invention that is described below.

The present invention further provides a method for preparing a polyglycerol partial ester, comprising the esterification of a polyglycerol with a) at least one polyhydroxycarboxylic acid of a hydroxycarboxylic acid having 8 to 32, preferably 12 to 22, particularly preferably 14 to 18, carbon atoms,
b) at least one short-chain dicarboxylic acid having 2 to 16, preferably 6 to 14, particularly preferably 8 to 12, carbon atoms,
c) at least one long-chain dicarboxylic acid having 24 to 44, preferably 30 to 40, particularly preferably 34 to 38, carbon atoms, and
d) at least one fatty acid selected from linear, unsaturated and branched, saturated fatty acids having 14 to 24, preferably 16 to 20, carbon atoms, preferably up to a degree of esterification from 35 to 95%, preferably from 40 to 90%,
particularly preferably from 45 to 85%, of all OH groups present in the polyglycerol partial ester, including the ones present in the polyhydroxycarboxylic acid.

According to the invention, the esterification of the various components a) to d) with the polyglycerol can take place simultaneously or sequentially in any desired order, simultaneously being preferred according to the invention.

According to the invention, in method step d), preference is given to carrying out esterification up to an acid number of the obtained polyglycerol partial ester within the range from 30 to 0, preferably from 15 to 0, particularly preferably from 5 to 0, mg KOH/g.

In preferred alternatives of the method according to the invention, the method according to the invention comprises the method steps A1) esterification of a polyglycerol with
a) at least one polyhydroxycarboxylic acid of a hydroxycarboxylic acid having 8 to 32, preferably 12 to 22, particularly preferably 14 to 18, carbon atoms and
d) at least one fatty acid selected from linear, unsaturated and branched, saturated fatty acids having 14 to 24, preferably 16 to 20, carbon atoms,
preferably up to an acid number of the polyglycerol partial ester obtained in this step within a range from 30 to 0, preferably from 15 to 0, particularly preferably from 5 to 0, mg KOH/g, and B1) esterification of the method step product from A1) with b) at least one short-chain dicarboxylic acid having 2 to 16, preferably 6 to 14, particularly preferably 8 to 12, carbon atoms and c) at least one long-chain dicarboxylic acid having 24 to 44, preferably 30 to 40, particularly preferably 34 to 38, carbon atoms, preferably up to an acid number of the polyglycerol partial ester obtained in this step within a range from 30 to 0, preferably from 15 to 0, particularly preferably from 5 to 0, mg KOH/g, and preferably up to a degree of esterification from 35 to 95%, preferably from 40 to 90%, particularly preferably from 45 to 85%, of all OH groups present in the polyglycerol partial ester, including the ones present in the polyhydroxycarboxylic acid, or A2) esterification of a polyglycerol with b) at least one short-chain dicarboxylic acid having 2 to 16, preferably 6 to 14, particularly preferably 8 to 12, carbon atoms, c) at least one long-chain dicarboxylic acid having 24 to 44, preferably 30 to 40, particularly preferably 34 to 38, carbon atoms, and d) at least one fatty acid selected from linear, unsaturated and branched, saturated fatty acids having 14 to 24, preferably 16 to 20, carbon atoms, preferably up to an acid number of the polyglycerol partial ester obtained in this step within a range from 30 to 0, preferably from 15 to 0, particularly preferably from 5 to 0, mg KOH/g, and B2) esterification of the method step product from A2) with a) at least one polyhydroxycarboxylic acid of a hydroxycarboxylic acid having 8 to 32, preferably 12 to 22, particularly preferably 14 to 18, carbon atoms, preferably up to an acid number of the polyglycerol partial ester obtained in this step within a range from 30 to 0, preferably from 15 to 0, particularly preferably from 5 to 0, mg KOH/g, and preferably up to a degree of esterification from 35 to 95%, preferably from 40 to 90%, particularly preferably from 45 to 85%, of all OH groups present in the polyglycerol partial ester, including the ones present in the polyhydroxycarboxylic acid.

The present invention further provides cosmetic or pharmaceutical preparations comprising at least one polyglycerol partial ester according to the invention and/or one polyglycerol partial ester obtainable in accordance with the method according to the invention, especially in an amount from 0.5% by weight to 20% by weight, preferably from 1% by weight to 10% by weight, wherein the percentages by weight are based on the total preparation.

Preferred preparations according to the invention are quick-break emulsions. Quick-breaking water-in-oil emulsions (so-called quick-break emulsions) are known as emulsions having a high water content that break very quickly as a result of the shear forces occurring during use and release water droplets, which are sometimes visible, while doing so.

Consequently, preferred quick-break emulsions according to the invention contain an internal aqueous phase in an amount from 80% by weight to 94.5% by weight, preferably from 83% by weight to 92% by weight, an external oil phase in an amount from 5% by weight to 20% by weight, preferably from 8% by weight to 17% by weight, and the at least one polyglycerol partial ester according to the invention and/or the one polyglycerol partial ester obtainable in accordance with the method according to the invention in an amount from 0.5% by weight to 2.0% by weight, preferably from 0.5% by weight to 1.5% by weight, wherein the percentages by weight are based on the total preparation.

Preferably, the preparations according to the invention are PEG-free. This is to be understood to mean that, according to the invention, it is possible to dispense with the addition of polyethylene glycols and/or polyethylene glycol derivatives, such as, for example, ethoxylated esters, fatty acid or fatty alcohols. Therefore, the fraction of PEG-containing substances is below 1% by weight, based on the total mass of the preparation, in order to be considered PEG-free according to the invention. Preferably, the fraction of PEG-containing substances is 0% by weight.

The present invention further provides for the use of at least one polyglycerol partial ester according to the invention and/or one polyglycerol partial ester obtainable in accordance with the method according to the invention as W/O emulsifier, especially in cosmetic or pharmaceutical preparations, and for the use of at least one polyglycerol partial ester according to the invention and/or one polyglycerol partial ester obtainable in accordance with the method according to the invention for preparing quick-break emulsions.

The examples adduced hereinafter describe the present invention by way of example, without any intention that the invention, the scope of application of which is apparent from the entirety of the description and the claims, be restricted to the embodiments specified in the examples.

EXAMPLES

Example 1: PGE, Inventive

A mixture of polyglycerol (OHN=1113 mg KOH/g, 52.3 g, 0.188 mol), oleic acid (Palmera A1818 from KLK Emmerich GmbH, AN=200 mg KOH/g, iodine number=92.3 g 12/100 g, 91.1 g, 0.325 mol), sebacic acid (17.0 g, 0.084 mol), dimer acid (Radiacid 0977 from Oleon having about 36 carbon atoms, functionality=2.0, AN=191 mg KOH/g, 42.6 g, 0.074 mol) and polyhydroxystearic acid (AN=48 mg KOH/g, 140.1 g, 0.120 mol) was heated to 240° C. with stirring and the water which formed was continuously distilled off until an acid number of 5 mg KOH/g was attained. Acid number: 5 mg KOH/g; hydrolysis number: 177 mg KOH/g; hydroxyl number: 55 mg KOH/g; degree of esterification: 76%.

Example 2: PGE, Inventive

A mixture of polyglycerol (OHN=1073 mg KOH/g, 52.3 g, 0.167 mol), oleic acid (Palmera A1818 from KLK Emmerich GmbH, AN=200 mg KOH/g, iodine number=92.3 g 12/100 g, 100.0 g, 0.357 mol) and polyhydroxystearic acid (AN=52 mg KOH/g, 120.2 g, 0.111 mol) was heated to 240° C. with stirring and the water which formed was continuously distilled off until an acid number of 8 mg KOH/g was attained. After addition of sebacic acid (18.3 g, 0.090 mol) and dimer acid (Radiacid 0977 from Oleon having about 36 carbon atoms, functionality=2.0, AN=193.5 mg KOH/g, 38.2 g, 0.066 mol), the mixture was further heated to 240° C. with stirring and the water which formed was continuously distilled off until an acid number of 2 mg KOH/g was attained. Acid number: 2 mg KOH/g; hydrolysis number: 181 mg KOH/g; hydroxyl number: 48 mg KOH/g; degree of esterification: 79%.

Example 3: PGE, Inventive

A mixture of polyglycerol (OHN=1024 mg KOH/g, 63.0 g, 0.170 mol), sebacic acid (12.0 g, 0.059 mol) and dimer acid (Radiacid 0977 from Oleon having about 36 carbon atoms, functionality=2.0, AN=193.5 mg KOH/g, 48.2 g, 0.084 mol) was heated to 240° C. with stirring and the water which formed was continuously distilled off until an acid number of 11 mg KOH/g was attained. After addition of oleic acid (Palmera A1818 from KLK Emmerich GmbH, AN=200 mg KOH/g, iodine number=92.3 g 12/100 g, 75.4 g, 0.269 mol) and polyhydroxystearic acid (AN=42 mg KOH/g, 100.0 g, 0.075 mol), the mixture was further heated to 240° C. with stirring and the water which formed was continuously distilled off until an acid number of 3 mg KOH/g was attained. Acid number: 3 mg KOH/g; hydrolysis number: 164 mg KOH/g; hydroxyl number: 110 mg KOH/g; degree of esterification: 59%.

Example 4: PGE, Inventive

A mixture of polyglycerol (OHN=1136 mg KOH/g, 52.5 g, 0.201 mol), oleic acid (Palmera A1818 from KLK Emmerich GmbH, AN=200 mg KOH/g, iodine number=92.3 g 12/100 g, 90.0 g, 0.321 mol), sebacic acid (16.0 g, 0.079 mol) and dimer acid (Radiacid 0977 from Oleon having about 36 carbon atoms, functionality=2.0, AN=191 mg KOH/g, 46.4 g, 0.081 mol) was heated to 240° C. with stirring and the water which formed was continuously distilled off until an acid number of 5 mg KOH/g was attained. After addition of polyhydroxystearic acid (AN=48 mg KOH/g, 140.4 g, 0.120 mol), the mixture was further heated to 240° C. with stirring and the water which formed was continuously distilled off until an acid number of 2 mg KOH/g was attained. Acid number: 2 mg KOH/g; hydrolysis number: 178 mg KOH/g; hydroxyl number: 57 mg KOH/g; degree of esterification: 76%.

Example 5: PGE, Inventive

A mixture of polyglycerol (OHN=1040 mg KOH/g, 67.6 g, 0.193 mol), isostearic acid (94.8 g, 0.325 mol), sebacic acid (17.4 g, 0.086 mol), dimer acid (Radiacid 0977 from Oleon having about 36 carbon atoms, functionality=2.0, AN=191 mg KOH/g, 37.3 g, 0.065 mol) and polyhydroxystearic acid (AN=48 mg KOH/g, 120.0 g, 0.103 mol) was heated to 240° C. with stirring and the water which formed was continuously distilled off until an acid number of 3 mg KOH/g was attained. Acid number: 3 mg KOH/g; hydrolysis number: 167 mg KOH/g; hydroxyl number: 95 mg KOH/g; degree of esterification: 63%.

Example 6: PGE, Inventive

A mixture of polyglycerol (OHN=1070 mg KOH/g, 65.0 g, 0.206 mol), isostearic acid (91.1 g, 0.312 mol) and sebacic acid (16.9 g, 0.084 mol) was heated to 240° C. with stirring and the water which formed was continuously distilled off until an acid number of 0.4 mg KOH/g was attained. After addition of dimer acid (Radiacid 0977 from Oleon having about 36 carbon atoms, functionality=2.0, AN=193.5 mg KOH/g, 35.4 g, 0.062 mol), the mixture was further heated to 240° C. with stirring and the water which formed was continuously distilled off until an acid number of 0.8 mg KOH/g was attained. After addition of polyhydroxystearic acid (AN=45 mg KOH/g, 135.0 g, 0.108 mol), the mixture was further heated to 240° C. with stirring and the water which formed was continuously distilled off until an acid number of 1.0 mg KOH/g was attained. Acid number: 1 mg KOH/g; hydrolysis number: 171 mg KOH/g; hydroxyl number: 93 mg KOH/g; degree of esterification: 65%.

Example 7: PGE, Inventive

A mixture of polyglycerol (OHN=1107 mg KOH/g, 50.5 g, 0.179 mol), oleic acid (Mascid 1318 from ICOF Europe, AN=199 mg KOH/g, iodine number=92.7 g 12/100 g, 89.0 g, 0.317 mol), sebacic acid (16.6 g, 0.082 mol), dimer acid (Radiacid 0977 from Oleon having about 36 carbon atoms, functionality=2.0, AN=193.5 mg KOH/g, 44.6 g, 0.078 mol) and polyricinoleic acid (AN=45 mg KOH/g, 144.1 g, 0.116 mol) was heated to 240° C. with stirring and the water which formed was continuously distilled off until an acid number of 2.5 mg KOH/g was attained. Acid number: 2.5 mg KOH/g; hydrolysis number: 196 mg KOH/g; hydroxyl number: 50 mg KOH/g; degree of esterification: 79%.

Example 8: PGE, Inventive

A mixture of polyglycerol (OHN=1113 mg KOH/g, 59.5 g, 0.178 mol), isostearic acid (90.3 g, 0.310 mol), sebacic acid (15.0 g, 0.074 mol), dimer acid (Radiacid 0977 from Oleon having about 36 carbon atoms, functionality=2.0, AN=193.5 mg KOH/g, 46.2 g, 0.080 mol) and polyhydroxystearic acid (AN=47 mg KOH/g, 133.1 g, 0.111 mol) was heated to 240° C. with stirring and the water which formed was continuously distilled off until an acid number of 1.2 mg KOH/g was attained. Acid number: 1.2 mg KOH/g; hydrolysis number: 188 mg KOH/g;
hydroxyl number: 49 mg KOH/g; degree of esterification: 79%.

Example 9: PGE, Inventive

A mixture of polyglycerol (OHN=1107 mg KOH/g, 50.5 g, 0.179 mol), isostearic acid (75.0 g, 0.257 mol), sebacic acid (14.0 g, 0.069 mol), dimer acid (Radiacid 0977 from Oleon having about 36 carbon atoms, functionality=2.0, AN=193.5 mg KOH/g, 40.0 g, 0.070 mol) and polyricinoleic acid (AN=45 mg KOH/g, 154.1 g, 0.124 mol) was heated to 240° C. with stirring and the water which formed was continuously distilled off until an acid number of 2.4 mg KOH/g was attained. Acid number: 2.4 mg KOH/g; hydrolysis number: 193 mg KOH/g; hydroxyl number: 48 mg KOH/g; degree of esterification: 80%.

Example 10: PGE, Inventive

A mixture of a first polyglycerol (OHN=1165 mg KOH/g, 25.3 g, 0.104 mol), a second polyglycerol (OHN=967 mg KOH/g, 27.6 g, 0.058 mol), oleic acid (Mascid 1318 from ICOF Europe, AN=199 mg KOH/g, iodine number=92.7 g $I_2$/100 g, 91.1 g, 0.325 mol), sebacic acid (17.0 g, 0.084 mol), dimer acid (Radiacid 0977 from Oleon having about 36 carbon atoms, functionality=2.0, AN=193.5 mg KOH/g, 42.6 g, 0.074 mol) and polyhydroxystearic acid (AN=48 mg KOH/g, 140.1 g, 0.120 mol) was heated to 240° C. with stirring and the water which formed was continuously distilled off until an acid number of 5 mg KOH/g was attained. Acid number: 5 mg KOH/g; hydrolysis number: 177 mg KOH/g; hydroxyl number: 48 mg KOH/g; degree of esterification: 78%.

Example 11: PGE, Inventive

A mixture of polyglycerol (OHN=1113 mg KOH/g, 52.3 g, 0.188 mol), oleic acid (Mascid 1318 from ICOF Europe, AN=199 mg KOH/g, iodine number=92.7 g 12/100 g, 45.0 g, 0.161 mol), isostearic acid (47.9 g, 0.164 mol), sebacic acid (17.0 g, 0.084 mol), dimer acid (Radiacid 0977 from Oleon having about 36 carbon atoms, functionality=2.0, AN=191 mg KOH/g, 42.6 g, 0.074 mol) and polyhydroxystearic acid (AN=48 mg KOH/g, 140.1 g, 0.120 mol) was heated to 240° C. with stirring and the water which formed was continuously distilled off until an acid number of 5 mg KOH/g was attained. Acid number: 5 mg KOH/g; hydrolysis number: 178 mg KOH/g; hydroxyl number: 54 mg KOH/g; degree of esterification: 76%.

Example 12: PGE with PHA, Oleic Acid, Only Short-Chain Dicarboxylic Acid, Non-Inventive A mixture of polyglycerol (OHN=1124 mg KOH/g, 48.2 g, 0.184 mol), oleic acid (Mascid 1318 from ICOF Europe, AN=199 mg KOH/g, iodine number=92.7 g 12/100 g, 80.1 g, 0.286 mol) and sebacic acid (14.9 g, 0.074 mol) was heated to 240° C. with stirring and the water which formed was continuously distilled off until an acid number of 1.5 mg KOH/g was attained. After addition of polyhydroxystearic acid (AN=49 mg KOH/g, 156.7 g, 0.137 mol), the mixture was further heated to 240° C. with stirring and the water which formed was continuously distilled off until an acid number of 2.5 mg KOH/g was attained. Acid number: 2.5 mg KOH/g; hydrolysis number: 187 mg KOH/g; hydroxyl number: 81 mg KOH/g; degree of esterification: 69%.

Example 13: PGE with PHA, Oleic Acid, Only Long-Chain Dicarboxylic Acid, Non-Inventive A mixture of polyglycerol (OHN=1124 mg KOH/g, 48.6 g, 0.186 mol), oleic acid (Mascid 1318 from ICOF Europe, AN=199 mg KOH/g, iodine number=92.7 g 12/100 g, 90.2 g, 0.322 mol) and dimer acid (Radiacid 0977 from Oleon having about 36 carbon atoms, functionality=2.0, AN=193.5 mg KOH/g, 42.7 g, 0.074 mol) was heated to 240° C. with stirring and the water which formed was continuously distilled off until an acid number of 2.3 mg KOH/g was attained. After addition of polyhydroxystearic acid (AN=49 mg KOH/g, 118.5 g, 0.103 mol), the mixture was further heated to 240° C. with stirring and the water which formed was continuously distilled off until an acid number of 2.5 mg KOH/g was attained. Acid number: 2.5 mg KOH/g; hydrolysis number: 170 mg KOH/g; hydroxyl number: 77 mg KOH/g; degree of esterification: 76%.

Example 14: PGE with PHA, Long- and Short-Chain Dicarboxylic Acid, Only Saturated Unbranched Fatty Acid, Non-Inventive A mixture of polyglycerol (OHN=1124 mg KOH/g, 43 g, 0.164 mol), stearic and palmitic acid in the ratio 46:54 (71 g, 0.263 mol), sebacic acid (11.6 g, 0.057 mol) and dimer acid (Radiacid 0977 from Oleon having about 36 carbon atoms, functionality=2.0, AN=193.5 mg KOH/g, 44.4 g, 0.077 mol) was heated to 240° C. with stirring and the water which formed was continuously distilled off until an acid number of 5 mg KOH/g was attained. After addition of polyhydroxystearic acid (AN=49 mg KOH/g, 130 g, 0.114 mol), the mixture was further heated to 240° C. with stirring and the water which formed was continuously distilled off until an acid number of 2.5 mg KOH/g was attained. Acid number: 2.5 mg KOH/g; hydrolysis number: 188 mg KOH/g; hydroxyl number: 53 mg KOH/g; degree of esterification: 78%.

Example 15: Differentiation of the Capacity for Emulsion Stabilization of the Inventive Examples with Respect to the Prior Art The example emulsions which follow are intended to illustrate the subject matter of the invention in detail, without restricting said subject matter to said examples.

All concentrations in the application examples are given in percent by weight. Customary homogenization processes known to the person skilled in the art were used to produce the emulsions.

The emulsions were produced using either a hot/cold process or a cold/cold process. In the hot/cold process, production was typically effected such that the oil phase was heated to 70-75° C. Thereafter, the water phase was stirred into the oil phase within about 2 minutes. After completion of stirring, a brief homogenization was carried out. After cooling of the emulsion below 30° C., a further homogenization was carried out for about 2 minutes. In the cold/cold process, the water phase was stirred into the oil phase at room temperature within about 2 minutes and the emulsion was then homogenized.

Further ingredients (such as, for example, preservatives, active ingredients) were added preferably below 40° C. and after the first homogenization. In the event of the formulations being preserved with organic acids, the pH of the water phase was adjusted to about 5.

These experiments are intended to show that the polyglycerol esters according to the invention have advantages with regard to emulsion stability. The non-inventive emulsifiers corresponding to Examples 12-14 were selected here as representatives of polyglycerol-based W/O emulsifiers based on the prior art.

To test the storage stability of the emulsions, these were stored for one month at room temperature and 45° C. To test the low-temperature stability, three freeze-thaw cycles of 25° C./−15° C./25° C. were carried out. Considerable changes in the appearance or the consistency, and in particular oil or water separations, were weighted as criteria for instability. The reported emulsion viscosities were determined at room temperature 3 days after emulsion production using a Brookfield RVT, spindle C, 10 rpm (cream) or spindle 5, 10 rpm (lotion).

Comparison of the inventive emulsifiers according to Examples 1, 3, 5 and 7 against the non-inventive emulsifiers according to Examples 12-14 was done in three different formulations: 1—lotion (cold/cold), 2—cream (hot/cold), 3—quick-break cream (cold/cold). These systems are intended to show that, in contrast to the prior art represented by the emulsifiers according to Synthesis Examples 12-14, it is possible with the inventive emulsifiers to stabilize emulsions across a large viscosity range. Formulation 3 in particular represents an extreme challenge for the emulsifier owing to the large internal water phase.

Lotion

| Formulation | 1 |
|---|---|
| Emulsifier | 2.0 |
| Beeswax | 0.5 |
| Castor wax | 0.5 |
| Paraffinum perliquidum | 10.5 |
| Decyl cocoate[1] | 8.0 |
| Tocopheryl acetate | 0.5 |
| Cyclopentasiloxane | 6.0 |
| Sodium chloride | 0.5 |
| Water | to 100 |
| Glycerol | 3.0 |
| Phenoxyethanol; ethylhexylglycerol[2] | 0.7 |
| Ethanol | 5.0 |

[1] TEGOSOFT® DC (Evonik Industries AG)
[2] Euxyl PE 9010 (Schülke & Mayr GmbH)

Cream

| Formulation | 2 |
|---|---|
| Emulsifier | 2.0 |
| Mineral oil | 17.0 |
| Castor wax | 0.4 |
| Microcrystalline wax | 0.6 |
| Water | to 100 |
| Sodium chloride | 0.5 |
| Urea | 10.0 |
| Phenoxyethanol; ethylhexylglycerol[2] | 0.7 |

Quick-Breaking Cream

| Formulation | 3 |
|---|---|
| Emulsifier | 0.8 |
| Cetyl dimethicone[3] | 1.6 |
| Diethylhexyl carbonate[4] | 4.0 |
| Dimethicone[5] | 1.0 |
| Cyclopentasiloxane | 4.0 |
| Magnesium stearate | 0.3 |
| Water | to 100 |
| Propylene glycol | 5.0 |
| Sodium chloride | 1.0 |
| Methylisothiazolinone, methylparaben, ethylparaben; dipropylene glycol[6] | 0.8 |

[3] ABIL® Wax 9801 (Evonik Industries AG)
[4] TEGOSOFT® DEC (Evonik Industries AG)
[5] ABIL® 350 (Evonik Industries AG)
[6] Microcare MEM (Thor)

TABLE 1

| Formulation | | Emulsifier as per Ex. | Viscosity | Emulsion stability with storage at | | |
|---|---|---|---|---|---|---|
| | | | | room temperature | warm temperature | cold temperature |
| Formulation 1 Lotion | | 1 | 14 | Stable | Stable | Stable |
| | | 3 | 15 | Stable | Stable | Stable |
| | | 5 | 14 | Stable | Stable | Stable |
| | | 7 | 12 | Stable | Stable | Stable |
| | | 12 | 12 | Stable | Water separation | Stable |
| | | 13 | 14 | Stable | Water separation | Stable |
| | | 14 | 17 | Stable | Stable | Phase separation |
| Formulation 2 Cream | | 1 | 78 | Stable | Stable | Stable |
| | | 3 | 76 | Stable | Stable | Stable |
| | | 5 | 61 | Stable | Stable | Stable |
| | | 7 | 72 | Stable | Stable | Stable |
| | | 12 | 33 | Water separation, Drop in viscosity | Water separation | Stable |
| | | 13 | 38 | Drop in viscosity | Water separation | Stable |
| | | 14 | 71 | Stable | Stable | Stable |
| Formulation 3 Quick-breaking cream | | 1 | 72 | Stable | Stable | Stable |
| | | 3 | 72 | Stable | Stable | Stable |
| | | 5 | 78 | Stable | Stable | Stable |
| | | 7 | 67 | Stable | Stable | Stable |
| | | 12 | 54 | Stable | Water separation | Stable |
| | | 13 | 58 | Stable | Water separation | Stable |
| | | 14 | 63 | Stable | Stable | Water separation |

As can be gathered from Table 1, only the inventive emulsifiers stabilize Formulations 1-3 in the required manner. The prior-art-corresponding emulsifiers according to Synthesis Examples 12-14 show, depending on the formulation and the emulsifier makeup, distinct and unacceptable weaknesses with respect to emulsion stabilization for the different stability criteria. In addition, access to quick-breaking systems with the emulsifiers according to the invention is surprising, since quick-breaking systems are not accessible with emulsifiers claimed in the specifications EP 1 683 781, EP 1 500 427 and EP 0 835 862.

Example 16: Differentiation of the Sensory Properties of the Inventive Examples with Respect to the Prior Art Formulations 3a to 3d were prepared for the differentiation of the sensory properties of the emulsifiers according to the invention with respect to the prior art. The effect on the skin feel of the formulations was investigated by means of a panel test. Six individuals each applied a defined amount of about 25 µL of the four formulations to a defined test area on the inner side of the forearm, without knowing the composition of the formulations. The formulations were distributed in the test area by circulating movements using a finger. An initial assessment of sensory properties is made. There was then a pause for 5 minutes, and the skin feel on the test area was subsequently reassessed.

| Formulation | 3a | 3b | 3c | 3d |
|---|---|---|---|---|
| Emulsifier as per Ex. 1 | 2.5 | — | — | — |
| Emulsifier as per EP 1 683 781 | — | 2.5 | — | — |
| Emulsifier as per EP 1 500 427 | — | — | 2.5 | — |
| Emulsifier as per EP 0 835 862 | — | — | — | 2.5 |
| Zinc stearate | 0.5 | 0.5 | 0.5 | 0.5 |
| Ethylhexyl stearate | 7.0 | 7.0 | 7.0 | 7.0 |
| Isohexadecane | 7.0 | 7.0 | 7.0 | 7.0 |
| Cetearyl ethylhexanoate | 7.0 | 7.0 | 7.0 | 7.0 |
| Water | to 100 | to 100 | to 100 | to 100 |
| Sodium chloride | 0.5 | 0.5 | 0.5 | 0.5 |
| Phenoxyethanol; ethylhexylglycerol[2] | 0.7 | 0.7 | 0.7 | 0.7 |

The results of the assessment of the skin feel are shown in Table 2. What are listed are those sensory properties which differ in terms of their characteristics between the four emulsions.

TABLE 2

| Sensory property | Formulation 3a inventive | Formulation 3b not inventive | Formulation 3c not inventive | Formulation 3d not inventive |
|---|---|---|---|---|
| Initial absorption | High absorption | Medium absorption | Medium absorption | Medium to low absorption |
| Oiliness after 5 min | Low oiliness | Medium oiliness | Medium oiliness | Medium oiliness |
| Absorption after 5 min | Very high absorption | High absorption | High absorption | High absorption |

Formulation 3a differs from formulations 3b to 3d by a higher absorption, both initially and after 5 min, and by lower oiliness, this being equivalent to a lighter, better skin feel. In this respect, this is surprising for a person skilled in the art, since use of additional polyfunctional fatty acids in emulsifiers generates a higher molecular weight and a heavier, poorer skin feel in the emulsion is typically associated therewith, this becoming apparent in increased oiliness and reduced absorption.

FORMULATION EXAMPLES

The examples below are intended to show that the polyglycerol esters according to the invention can be used in a large number of cosmetic formulations.

Moreover, with the help of the emulsifiers according to the invention, it is possible to stably incorporate pigments or solids into emulsion preparations.

Furthermore, the examples show good compatibility with typical coemulsifiers, oils, waxes and stabilizers, as well as good compatibility with emulsion-loading ingredients such as UV filters, antimicrobial active ingredients, electrolytes or cosmetic active ingredients.

Cooling Body Lotion

| Formulation | 4a | 4b |
|---|---|---|
| Emulsifier as per Ex. 1 | 2.0 | 1.5 |
| Polyglyceryl-4 diisostearate/polyhydroxystearate/sebacate[7] | — | 0.5 |
| Castor wax | 0.5 | 0.5 |
| Beeswax | 0.5 | 0.5 |
| Ethylhexyl stearate[8] | 10.0 | 10.0 |
| Diethylhexyl carbonate[4] | 8.5 | 8.5 |
| Dimethicone[9] | 6.0 | 6.0 |
| Tocopheryl acetate | 0.5 | 0.5 |
| Glycerol | 3.0 | 3.0 |
| Water | to 100 | to 100 |
| Sodium chloride | 1.0 | 1.0 |
| Ethanol | 20.0 | 20.0 |

[7] ISOLAN ® GPS (Evonik Industries AG)
[8] TEGOSOFT ® OS (Evonik Industries AG)
[9] Belsil DM 5 (Wacker Chemical Corp.)

W/O Cream Based on Natural Ingredients

| Formulation | 5a | 5b |
|---|---|---|
| Emulsifier as per Ex. 3 | 3.0 | 2.5 |
| Diisostearyl polyglyceryl-3 dimer dilinoleate[10] | — | 0.5 |
| Diethylhexyl carbonate[4] | 7.0 | 7.0 |
| Oleyl erucate[11] | 3.0 | 3.0 |
| Almond oil | 7.0 | 7.0 |
| Shea butter | 2.0 | 2.0 |
| Cetyl ricinoleate[12] | 1.0 | 1.0 |
| Beeswax | 0.6 | 0.6 |
| Castor wax | 0.4 | 0.4 |
| Glycerol | 5.0 | 5.0 |
| Water | to 100 | to 100 |
| Magnesium sulphate heptahydrate | 1.5 | 1.5 |
| Sodium benzoate, potassium sorbate[13] | 0.5 | 0.5 |

[10] ISOLAN ® PDI (Evonik Industries AG)
[11] TEGOSOFT ® OER (Evonik Industries AG)
[12] TEGOSOFT ® CR (Evonik Industries AG)
[13] Euxyl K 712 (Schulke & Mayr GmbH)

Cold-Preparable Lotion

| Formulation | 6a | 6b | 6c | 6d |
|---|---|---|---|---|
| Emulsifier as per Ex. 2 | 3.0 | 3.0 | 2.5 | 2.5 |
| Polyglyceryl-3 oleate[14] | — | — | 0.5 | 0.5 |
| Isoamyl cocoate[15] | 5.0 | 5.00 | 5.0 | 5.0 |
| Diethylhexyl carbonate[4] | 12.0 | 12.0 | 12.0 | 12.0 |
| Phenoxyethyl caprylate[16] | 4.0 | 4.0 | 4.0 | 4.0 |
| Zinc stearate | 0.5 | 0.5 | 0.5 | 0.5 |
| Water | to 100 | to 100 | to 100 | to 100 |
| Glycerol | 3.0 | 3.0 | 3.0 | 3.0 |
| Sodium chloride | 1.5 | 7.0 | 1.5 | 7.0 |
| Phenoxyethanol; ethylhexylglycerol[2] | 0.7 | 0.7 | 0.7 | 0.7 |

[14] ISOLAN ® GO 33 (Evonik Industries AG)
[15] TEGOSOFT ® AC (Evonik Industries AG)
[16] TEGOSOFT ® XC (Evonik Industries AG)

Moisturizing Lotion Containing Urea

| Formulation | 7a | 7b |
|---|---|---|
| Emulsifier as per Ex. 2 | 2.0 | 1.5 |
| Cetyl PEG/PPG-10/1 dimethicone[17] | — | 0.5 |
| Microcrystalline wax | 0.5 | 0.5 |
| Castor wax | 0.5 | 0.5 |
| C12-15 Alkyl benzoate | 7.5 | 7.5 |
| Oleyl erucate[11] | 5.0 | 5.0 |
| Ethylhexyl palmitate[18] | 5.0 | 5.0 |
| Caprylic/capric triglyceride | 5.0 | 5.0 |
| Glycerol | 3.0 | 3.0 |
| Urea | 20.0 | 20.0 |
| Magnesium sulphate heptahydrate | 1.0 | 1.0 |
| Water | to 100 | to 100 |
| Phenoxyethanol; ethylhexylglycerol[2] | 0.70 | 0.70 |
| Perfume | 0.10 | 0.10 |

[17] ABIL ® EM 180 (Evonik Industries AG)
[18] TEGOSOFT ® OP (Evonik Industries AG)

W/O Lotion with Light-as-Silk Skin Feel

| Formulation | 8a | 8b | 8c |
|---|---|---|---|
| Emulsifier as per Ex. 4 | 2.5 | 2.0 | 2.0 |
| Cetyl PEG/PPG-10/1 dimethicone[19] | — | 0.5 | — |
| Bis-PEG/PPG-14/14 dimethicone; dimethicone[20] | — | — | 1.0 |
| Microcrystalline wax | 0.1 | 0.1 | 0.1 |
| Castor wax | 0.1 | 0.1 | 0.1 |
| Diethylhexyl carbonate[4] | 11.8 | 11.8 | 11.8 |
| Myristyl myristate[21] | 1.0 | 1.0 | 1.0 |
| Dimethicone[9] | 8.0 | 8.0 | 8.0 |
| Dimethicone[5] | 0.5 | 0.5 | 0.5 |
| Glycerol | 3.0 | 3.0 | 3.0 |

-continued

| Formulation | 8a | 8b | 8c |
|---|---|---|---|
| Magnesium sulphate heptahydrate | 1.5 | 1.5 | 1.5 |
| Water | to 100 | to 100 | to 100 |
| Benzyl alcohol; ethylhexylglycerol; tocopherol[22] | 0.7 | 0.7 | 0.7 |

[19]ABIL ® EM 90 (Evonik Industries AG)
[20]ABIL ® EM 97 S (Evonik Industries AG)
[21]TEGOSOFT ® MM (Evonik Industries AG)
[22]Euxyl K 900 (Schulke & Mayr GmbH)

Baby-Care Product

| Formulation | 9a | 9b |
|---|---|---|
| Emulsifier as per Ex. 1 | 3.0 | 2.0 |
| Paraffinum liquidum; petrolatum; ozokerite; glyceryl oleate; lanolin alcohol[23] | — | 1.0 |
| Castor wax | 0.1 | 0.1 |
| Microcrystalline wax | 0.1 | 0.1 |
| Oleyl erucate[11] | 1.0 | 1.0 |
| Isoamyl cocoate[15] | 3.8 | 3.8 |
| Ethylhexyl palmitate[18] | 1.0 | 1.0 |
| Almond oil | 1.0 | 1.0 |
| Zinc oxide | 20.0 | 20.0 |
| Glycerol | 3.0 | 3.0 |
| Magnesium sulphate heptahydrate | 1.0 | 1.0 |
| Sodium lactate; sodium PCA; glycine; fructose; urea; niacinamide; inositol; sodium benzoate; lactic acid[24] | 5.0 | 5.0 |
| Betaine[25] | 3.0 | 3.0 |
| Water | to 100 | to 100 |
| Benzyl alcohol; ethylhexylglycerol; tocopherol[22] | 0.7 | 0.7 |

[23]PROTEGIN ® XN (Evonik Industries AG)
[24]LACTIL ® (Evonik Industries AG)
[25]TEGO ® Natural Betaine (Evonik Industries AG)

Foot-Care Product

| Formulation | 10a | 10b |
|---|---|---|
| Emulsifier as per Ex. 5 | 3.0 | 2.5 |
| Petrolatum; ozokerite; hydrogenated castor oil; glyceryl isostearate; polyglyceryl-3 oleate[26] | — | 0.5 |
| Castor wax | 0.1 | 0.1 |
| Microcrystalline wax | 0.1 | 0.1 |
| Diethylhexyl carbonate[4] | 9.0 | 9.0 |
| Ethylhexyl palmitate[18] | 9.0 | 9.0 |
| Stearyl heptanoate[27] | 8.8 | 8.8 |
| Glycerol | 3.0 | 3.0 |
| Magnesium sulphate heptahydrate | 1.0 | 1.0 |
| Ceramide NP; ceramide AP; ceramide EOP; phytosphingosine; cholesterol; sodium lauroyl lactylate; carbomer; xanthan gum[28] | 5.0 | 5.0 |
| Betaine[25] | 3.0 | 3.0 |
| Water | to 100 | to 100 |
| Benzyl alcohol; ethylhexylglycerol; tocopherol[22] | 0.7 | 0.7 |

[26]PROTEGIN ® W (Evonik Industries AG)
[27]EGOSOFT ® SH (Evonik Industries AG)
[28]SK-INFLUX ® V (Evonik Industries AG)

Sunscreen Lotion SPF 30 UVA with Insect Repellent

| Formulation | 11a | 11b |
|---|---|---|
| Emulsifier as per Ex. 3 | 3.0 | 2.0 |
| Polyglyceryl-2 dipolyhydroxystearate[29] | — | 1.0 |
| Oleyl erucate[11] | 1.5 | 1.5 |
| Diethylhexyl carbonate[4] | 1.5 | 1.5 |
| Diethylamino hydroxybenzoyl hexyl benzoate[30] | 5.4 | 5.4 |
| Ethylhexyl methoxycinnamate | 10.0 | 10.0 |
| Octocrylene | 2.0 | 2.0 |
| Polyacrylamide; C13-14 isoparaffin; laureth-7[31] | 2.1 | 2.1 |
| Ethyl butylacetylaminopropionate[32] | 4.0 | 4.0 |
| Tocopheryl acetate | 0.5 | 0.5 |
| Glycerol | 3.0 | 3.0 |
| Ethanol | 0.5 | 0.5 |
| Magnesium sulphate heptahydrate | 1.0 | 1.0 |
| Water | to 100 | to 100 |
| Benzyl alcohol; ethylhexylglycerol; tocopherol[22] | 0.7 | 0.7 |
| Perfume | 0.1 | 0.1 |

[29]Dehymuls PGPH (BASF SE)
[30]Uvinul A Plus (BASF SE)
[31]Sepigel 305 (Seppic)
[32]IR3535 (Merck KGaA)

Sunscreen Lotion SPF 30 UVA in Accordance with Ecocert Criteria

| Formulation | 12a | 12b |
|---|---|---|
| Emulsifier as per Ex. 1 | 3.0 | 2.0 |
| Polyglyceryl-3 polyricinoleate[33] | — | 1.0 |
| Isoamyl cocoate[15] | 2.0 | 2.0 |
| Decyl cocoate[1] | 10.0 | 10.0 |
| Isopropyl palmitate | 10.0 | 10.0 |
| Zinc oxide[34] | 16.0 | 16.0 |
| Titanium dioxide [nano]; alumina; stearic acid[35] | 9.0 | 9.0 |
| Water | to 100 | to 100 |
| Glycerol | 3.0 | 3.0 |
| Magnesium sulphate heptahydrate | 1.0 | 1.0 |
| Sodium benzoate, potassium sorbate[13] | 0.5 | 0.5 |

[33]Cithrol PG3PR (Croda Int. Plc)
[34]Zinc Oxide PI (Symrise)
[35]Eusolex T-S (Merck KGaA)

Sunscreen Spray SPF 30 UVA

| Formulation | 13a | 13b | 14a | 14b |
|---|---|---|---|---|
| Emulsifier as per Ex. 4 | 3.0 | 2.0 | 3.0 | 2.0 |
| Cetyl PEG/PPG-10/1 dimethicone[19] | — | 1.0 | — | — |
| Polyglyceryl-4 diisostearate/polyhydroxystearate/sebacate[7] | — | — | — | 1.0 |
| Diethylhexyl carbonate[4] | 13.0 | 13.0 | 11.3 | 11.3 |
| C12-15 Alkyl benzoate | 13.0 | 13.0 | 11.3 | 11.3 |
| Bis-ethylhexyloxyphenol methoxyphenyl triazine[36] | 1.0 | 1.0 | 1.5 | 1.5 |
| Butyl methoxydibenzoylmethane | — | — | 3.0 | 3.0 |
| Ethylhexyl methoxycinnamate | 5.0 | 5.0 | — | — |
| Octocrylene | — | — | 6.0 | 6.0 |
| Homosalate | — | — | 4.0 | 4.0 |
| Diethylamino hydroxybenzoyl hexyl benzoate[30] | 5.0 | 5.0 | — | — |

-continued

| Formulation | 13a | 13b | 14a | 14b |
|---|---|---|---|---|
| Water | to 100 | to 100 | to 100 | to 100 |
| Glycerol | 3.0 | 3.0 | 3.0 | 3.0 |
| Magnesium sulphate heptahydrate | 1.0 | 1.0 | 1.0 | 1.0 |
| UV filter solution[37] | 15.0 | 15.0 | 15.0 | 15.0 |
| Benzyl alcohol; ethylhexylglycerol; tocopherol[22] | 0.7 | 0.7 | 0.7 | 0.7 |

[36] Tinosorb S (BASF SE)
[37] 20% Phenylbenzimidazole sulphonic acid (Eusolex 232 (Merck KGaA)), 8.8% tris(hydroxymethyl)aminomethane, water to 100%

Sunscreen Lotion SPF 50 UVA

| Formulation | 15a | 15b | 16a | 16b |
|---|---|---|---|---|
| Emulsifier as per Ex. 4 | 3.0 | 2.5 | 3.0 | 2.5 |
| Cetyl PEG/PPG-10/1 dimethicone[17] | — | 1.0 | — | 1.0 |
| Microcrystalline wax | 0.3 | 0.3 | 0.3 | 0.3 |
| Castor wax | 0.3 | 0.3 | 0.3 | 0.3 |
| Diethylhexyl carbonate[4] | 2.4 | 2.4 | — | — |
| Phenoxyethyl caprylate[16] | — | — | 3.9 | 3.9 |
| Bis-ethylhexyloxyphenol methoxyphenyl triazine[36] | 6.0 | 6.0 | — | — |
| Diethylamino hydroxybenzoyl hexyl benzoate[30] | 7.0 | 7.0 | 5.0 | 5.0 |
| Butyl methoxydibenzoylmethane | — | — | 4.5 | 4.5 |
| Ethylhexyl salicylate | 3.0 | 3.0 | 5.0 | 5.0 |
| Ethylhexyl methoxycinnamate | 7.0 | 7.0 | — | — |
| Octocrylene | — | — | 9.0 | 9.0 |
| Homosalate | 3.0 | 3.0 | 5.0 | 5.0 |
| Ethylhexyl triazone[38] | 1.0 | 1.0 | 2.0 | 2.0 |
| Titanium dioxide; silica; dimethicone[39] | 2.0 | 2.0 | 2.0 | 2.0 |
| Water | to 100 | to 100 | to 100 | to 100 |
| Glycerol | 3.0 | 3.0 | 3.0 | 3.0 |
| Magnesium sulphate heptahydrate | 1.5 | 1.5 | 1.5 | 1.5 |
| Benzyl alcohol; ethylhexylglycerol; tocopherol[22] | 0.7 | 0.7 | 0.7 | 0.7 |

[38] Uvinul T 150 (BASF SE)
[39] Parsol TX (DSM Nutritional Products Llc.)

Sunscreen lotion SPF 50 in accordance with FDA criteria

| Formulation | 17a | 17b |
|---|---|---|
| Emulsifier as per Ex. 6 | 2.0 | 1.5 |
| Lauryl PEG-10 tris(trimethylsiloxy)silylethyl dimethicone[40] | — | 0.5 |
| Ethylhexyl methoxycinnamate; diethylamino hydroxybenzoyl hexyl benzoate[41] | 7.5 | 7.5 |
| Ethylhexyl salicylate | 5.0 | 5.0 |
| Homosalate | 15.0 | 15.0 |
| Butyl methoxydibenzoylmethane | 3.0 | 3.0 |
| Benzophenone-3 | 6.0 | 6.0 |
| Octocrylene | 10.0 | 10.0 |
| Triisostearin | 2.0 | 2.0 |
| Microcrystalline wax | 1.2 | 1.2 |
| Castor wax | 0.8 | 0.8 |
| Cetyl dimethicone[3] | 2.0 | 2.0 |
| Diethylhexyl carbonate[4] | 2.0 | 2.0 |
| Water | to 100 | to 100 |
| Sodium chloride | 1.0 | 1.0 |
| Ethylenediaminetetraacetic acid | 0.1 | 0.1 |
| Propylene glycol | 3.0 | 3.0 |
| Phenoxyethanol; ethylhexylglycerol[2] | 0.7 | 0.7 |

[40] ES-5300 Formulation Aid (Dow Corning Corp.)
[41] Uvinul A + B (BASF SE)

Foundation

| Formulation | 18a | 18b | 18c | 18d | 18e | 18f |
|---|---|---|---|---|---|---|
| Emulsifier as per Ex. 2 | 4.5 | 2.5 | 3.0 | 2.5 | 2.0 | 2.0 |
| Bis-(glyceryl/lauryl) glyceryl lauryl dimethicone; caprylic/capric triglyceride[42] | — | 2.0 | — | — | — | — |
| Polyglyceryl-4 isostearate[43] | — | — | 1.0 | — | — | — |
| Cetyl diglyceryl tris(trimethylsiloxy)silylethyl dimethicone[44] | — | — | — | 1.0 | — | — |
| Lauryl polyglyceryl-3 polydimethylsiloxyethyl dimethicone[45] | — | — | — | — | 1.0 | — |
| Polyglyceryl-4 isostearate; cetyl PEG/PPG-10/1 dimethicone; hexyl laurate[46] | — | — | — | — | — | 2.0 |
| Isoamyl cocoate[15] | 10.8 | 10.8 | 10.8 | 10.8 | 10.8 | 10.8 |
| Oleyl erucate[11] | 8.0 | 8.0 | 8.0 | 8.0 | 8.0 | 8.0 |
| Titanium dioxide, alumina, triethoxycaprylylsilane[47] | 4.0 | 4.0 | 4.0 | 4.0 | 4.0 | 4.0 |
| Iron oxides[48] | 2.1 | 2.1 | 2.1 | 2.1 | 2.1 | 2.1 |
| Nylon-12[49] | 2.0 | 2.0 | 2.0 | 2.0 | 2.0 | 2.0 |
| Cyclopentasiloxane | 3.5 | 3.5 | 3.5 | 3.5 | 3.5 | 3.5 |
| Disteardimonium hectorite[50] | 1.0 | 1.0 | 1.0 | 1.0 | 1.0 | 1.0 |
| Propylene carbonate | 0.5 | 0.5 | 0.5 | 0.5 | 0.5 | 0.5 |
| Water | to 100 | to 100 | to 100 | to 100 | to 100 | to 100 |
| Magnesium sulphate heptahydrate | 1.5 | 1.5 | 1.5 | 1.5 | 1.5 | 1.5 |
| Glycerol | 5.0 | 5.0 | 5.0 | 5.0 | 5.0 | 5.0 |
| Creatine[51] | 0.5 | 0.5 | 0.5 | 0.5 | 0.5 | 0.5 |
| Ceteareth-25; glycerol; cetyl alcohol; behenic acid; cholesterol; ceramide EOP; ceramide EOS; ceramide NP; ceramide NS; ceramide AP; caprooyl phytospingosine; caprooyl sphingosine[52] | 1.5 | 1.5 | 1.5 | 1.5 | 1.5 | 1.5 |
| Benzyl alcohol; ethylhexylglycerol; tocopherol[22] | 0.7 | 0.7 | 0.7 | 0.7 | 0.7 | 0.7 |

[42] ABIL® EM 120 (Evonik Industries AG)
[43] ISOLAN® GI 34 (Evonik Industries AG)
[44] DC-5600 (Dow Corning Corp.)
[45] KF-6105 (Shin-Etsu Chemical Co.)
[46] ABIL® WE 09 (Evonik Industries AG)
[47] Hombitan AC360 (Sachtleben)
[48] Sicovit Braun 70 E 172 (Rockwood)
[49] TEGOLON® 12-20 (Evonik Industries AG)
[50] Bentone 38 V CG (Elementis)
[51] TEGO® Cosmo C 100 (Evonik Industries AG)
[52] SKINMIMICS® (Evonik Industries AG)

CC (Colour Control) Fluid

| Formulation | 19a | 19b | 19c | 19d | 19e | 19f | 19g |
|---|---|---|---|---|---|---|---|
| Emulsifier as per Ex. 10 | 3.0 | 2.0 | 2.5 | 3.0 | 2.5 | 2.0 | 1.0 |
| Polyglyceryl-4 diisostearate/ polyhydroxystearate/ sebacate[7] | — | 1.0 | — | — | — | — | — |
| Sorbitan oleate[53] | — | — | 0.5 | — | — | — | — |
| PEG-30 dipolyhydroxystearate[54] | — | — | — | 1.0 | — | — | — |
| Polyglyceryl-3 diisostearate[55] | — | — | — | — | 1.5 | — | — |
| Glyceryl oleate, polyglyceryl-3 polyricinoleate, olea europaea (olive) oil unsaponifiables[56] | — | — | — | — | — | 1.0 | — |
| Lauryl PEG-9 polydimethylsiloxyethyl dimethicone[57] | — | — | — | — | — | — | 1.0 |
| Ethylhexyl methoxycinnamate; diethylamino hydroxybenzoyl hexyl benzoate[41] | 10.0 | 10.0 | 10.0 | 10.0 | 10.0 | 10.0 | 10.0 |
| Cyclopentasiloxane | 3.5 | 3.5 | 3.5 | 3.5 | 3.5 | 3.5 | 3.5 |
| Disteardimonium hectorite[50] | 1.0 | 1.0 | 1.0 | 1.0 | 1.0 | 1.0 | 1.0 |
| Propylene carbonate | 0.5 | 0.5 | 0.5 | 0.5 | 0.5 | 0.5 | 0.5 |
| Titanium dioxide, alumina, triethoxycaprylylsilane[47] | 4.0 | 4.0 | 4.0 | 4.0 | 4.0 | 4.0 | 4.0 |
| Talc | 2.0 | 2.0 | 2.0 | 2.0 | 2.0 | 2.0 | 2.0 |
| Iron oxides; triethoxycaprylylsilane[58] | 0.4 | 0.4 | 0.4 | 0.4 | 0.4 | 0.4 | 0.4 |
| Iron oxides; triethoxycaprylylsilane[59] | 0.12 | 0.12 | 0.12 | 0.12 | 0.12 | 0.12 | 0.12 |
| Iron oxides; triethoxycaprylylsilane[60] | 0.08 | 0.08 | 0.08 | 0.08 | 0.08 | 0.08 | 0.08 |
| Diethylhexyl carbonate[4] | 4.0 | 4.0 | 4.0 | 4.0 | 4.0 | 4.0 | 4.0 |
| C12-15 Alkyl benzoate | 4.0 | 4.0 | 4.0 | 4.0 | 4.0 | 4.0 | 4.0 |
| Isopropyl palmitate | 4.0 | 4.0 | 4.0 | 4.0 | 4.0 | 4.0 | 4.0 |
| Nylon-12[49] | 2.0 | 2.0 | 2.0 | 2.0 | 2.0 | 2.0 | 2.0 |
| Water | to 100 | to 100 | to 100 | to 100 | to 100 | to 100 | to 100 |
| Glycerol | 5.0 | 5.0 | 5.0 | 5.0 | 5.0 | 5.0 | 5.0 |
| Sodium chloride | 1.5 | 1.5 | 1.5 | 1.5 | 1.5 | 1.5 | 1.5 |
| Tetrapeptide-30; glycerol[61] | 0.3 | 0.3 | 0.3 | 0.3 | 0.3 | 0.3 | 0.3 |
| Phenoxyethanol; methyl paraben; ethylparaben; propylparaben[62] | 0.7 | 0.7 | 0.7 | 0.7 | 0.7 | 0.7 | 0.7 |

[53] TEGO® SMO V (Evonik Industries AG)
[54] Arlacel P135 (Croda)
[55] Lameform TGI (BASF SE)
[56] Plantasens Natural Emulsifier CP5 (Clariant)
[57] KF-6038 (Shin-Etsu Chemical Co.)
[58] Unipure Yellow LC 182 AS-EM (Sensient)
[59] Unipure Red LC 381 AS-EM (Sensient)
[60] Unipure Black LC 989 AS-EM (Sensient)
[61] TEGO Pep 4-Even (Evonik Industries AG)
[62] Phenonip XB (Clariant)

Antiperspirant/Deodorant Spray or Aerosol Spray

| Formulation | 20a | 20b | 20c | 20d |
|---|---|---|---|---|
| Emulsifier as per Ex. 1 | 3.0 | 2.0 | 3.0 | 2.0 |
| Polyglyceryl-4 diisostearate/ polyhydroxystearate/ sebacate[7] | — | 1.0 | — | 1.0 |
| Isopropyl palmitate | 20.0 | 20.0 | 20.0 | 20.0 |
| Diethylhexyl carbonate[4] | 7.0 | 7.0 | 7.0 | 7.0 |
| Water | to 100 | to 100 | to 100 | to 100 |
| Glycerol | 2.0 | 2.0 | 2.0 | 2.0 |
| Aluminium chlorohydrate (50% aq.) | 30.0 | 30.0 | 30.0 | 30.0 |
| Perfume | 1.0 | 1.0 | 1.0 | 1.0 |
| Propellant | — | — | Mix emulsions 20c-d with propellant in mass ratio of 5:2 | |

Sunscreen Aerosol SPF 50 UVA

| Formulation | 21a | 21b | 21c | 21d |
|---|---|---|---|---|
| Emulsifier as per Ex. 4 | 4.0 | 4.0 | 4.0 | 4.0 |
| Cetyl PEG/PPG-10/1 dimethicone[19)] | — | — | 1.0 | 1.0 |
| C12-15 Alkyl benzoate | 10.0 | 8.0 | 10.0 | 8.0 |
| Diethylhexyl carbonate[4)] | 13.0 | 10.0 | 13.0 | 10.0 |
| Bis-ethylhexyloxyphenol methoxyphenyl triazine[36)] | 4.0 | 4.0 | 4.0 | 4.0 |
| Diethylamino hydroxybenzoyl hexyl benzoate[30)] | 5.0 | 5.0 | 5.0 | 5.0 |
| Ethylhexyl salicylate | 5.0 | 5.0 | 5.0 | 5.0 |
| Ethylhexyl methoxycinnamate | 4.0 | 4.0 | 4.0 | 4.0 |
| Water | to 100 | to 100 | to 100 | to 100 |
| Glycerol | 3.0 | 3.0 | 3.0 | 3.0 |
| UV filter solution[37)] | 20.0 | 20.0 | 20.0 | 20.0 |
| Magnesium sulphate heptahydrate | 1.0 | 1.0 | 1.0 | 1.0 |
| Benzyl alcohol; ethylhexylglycerol; tocopherol[22)] | 0.7 | 0.7 | 0.7 | 0.7 |

Mix emulsions 21a-d with propellant in mass ratio of 2:1

W/O Quick-Breaking Cream Based on Natural Ingredients

| Formulation | 22 |
|---|---|
| Emulsifier as per Ex. 3 | 1.4 |
| Isoamyl cocoate[15)] | 5.0 |
| Decyl cocoate[1)] | 1.5 |
| Jojoba oil | 2.1 |
| Almond oil | 1.5 |
| Water | to 100 |
| Glycerol | 7.0 |
| Zinc sulphate heptahydrate | 1.5 |
| Sodium benzoate, potassium sorbate[13)] | 0.5 |

The invention claimed is:

1. A quick-break emulsion comprising
a polyglycerol partial ester obtained by esterification of a polyglycerol with a carboxylic acid mixture comprising:
   a) a polyhydroxycarboxylic acid of a hydroxycarboxylic acid having from 14 to 18 carbon atoms,
   b) at least one short-chain dicarboxylic acid having from 2 to 16 carbon atoms,
   c) at least one long-chain dicarboxylic acid having from 34 to 38 carbon atoms, and
   d) at least one fatty acid selected from linear, unsaturated and branched, saturated fatty acids having from 14 to 24 carbon atoms;
   wherein the polyglycerol comprises
      i. from 0 to 15% by weight of glycerol,
      ii. from 10 to 40% by weight of diglycerol,
      iii. from 10 to 50% by weight of triglycerol,
      iv. from 5 to 25% by weight of tetraglycerol, and
      v. from 0 to 55% by weight of pentaglycerol and higher glycerols;
   wherein the polyglycerol has a hydroxyl number of from 1520 to 845 and wherein the carboxylic acid mixture of a), b), c) and d) make up at least 80% by weight based on the total carboxylic acid mixture; and
   wherein, in the esterification, the molar ratio of b) to c) is from 0.5:1.0 to 1.0:0.5, and wherein the quick-break emulsion contains an internal aqueous phase of from 83% by weight to 94.5% by weight and an external oil phase in an amount of from 5% by weight to 17% by weight, and from 0.5% by weight to 2.0% by weight of the polyglycerol partial ester, wherein the % by weight is based on the total emulsion.

2. The quick-break emulsion according to claim 1, wherein the polyglycerol has an average degree of condensation of from 1.5 to 8, and wherein the polyglycerol has a hydroxyl number of from 1350 to 970, and wherein the carboxylic acid mixture of a), b), c) and d) make up at least 90% by weight based on the total carboxylic acid mixture.

3. The quick-break emulsion according to claim 1, wherein the polyhydroxycarboxylic acid is selected from the group consisting of polyhydroxystearic acid and polyricinoleic acid, and wherein the carboxylic acid mixture of a), b), c) and d) make up at least 95% by weight based on the total carboxylic acid mixture.

4. The quick-break emulsion according to claim 1, wherein the polyhydroxycarboxylic acid has an average degree of condensation of from 1.5 to 9, and wherein the polyglycerol has a hydroxyl number of from 1170 to 1010.

5. The quick-break emulsion according to claim 1, wherein the short-chain dicarboxylic acid is selected from the group consisting of aliphatic, linear dicarboxylic acids, oxalic acid, malonic acid, succinic acid, glutaric acid, adipic acid, pimelic acid, suberic acid, azelaic acid, sebacic acid, and dodecanedioic acid.

6. The quick-break emulsion according to claim 1, wherein the long-chain dicarboxylic acid is selected from the long-chain dicarboxylic acid obtainable from the dimerization of oleic acid and/or linoleic acid.

7. The quick-break emulsion according to claim 1, wherein the at least one fatty acid selected from linear, unsaturated and branched, saturated fatty acid is selected from the group consisting of isostearic acid, undecylenic acid, myristoleic acid, palmitoleic acid, petroselinic acid, oleic acid, elaidic acid, vaccenic acid, gadoleic acid, icosenoic acid, cetoleic acid, erucic acid, nervonic acid, linoleic acid, alpha-linolenic acid, gamma-linolenic acid, calendulic acid, punicic acid, alpha-elaeostearic acid, beta-elaeostearic acid, arachidonic acid, timnodonic acid, clupanodonic acid, and cervonic acid.

8. The quick-break emulsion according to claim 1, wherein the degree of esterification is from 35 to 95% of all OH groups present in the polyglycerol partial ester, including the ones present in the polyhydroxycarboxylic acid.

9. The quick-break emulsion according to claim 1, wherein, in the esterification,
   from 0.1 to 2 mol of a),
   from 0.1 to 2 mol of b),
   from 0.1 to 2 mol of c), and
   from 0.5 to 4 mol of d)
   are used per mole of polyglycerol.

10. The quick-break emulsion according to claim 1, wherein, in the esterification, the molar ratio of b) to c) is from 0.7:1.0 to 1.0:0.7.

11. A method for preparing a quick-break emulsion with a polyglycerol partial ester, comprising the esterification of a polyglycerol with a carboxylic acid mixture comprising:
   a) a polyhydroxycarboxylic acid of a hydroxycarboxylic acid having from 14 to 18 carbon atoms,
   b) a short-chain dicarboxylic acid having from 2 to 16 carbon atoms,
   c) a long-chain dicarboxylic acid having from 34 to 38 carbon atoms, and
   d) a fatty acid selected from linear, unsaturated and branched, saturated fatty acids having from 14 to 24 carbon atoms;

wherein the polyglycerol comprises
  i. from 0 to 15% by weight of glycerol,
  ii. from 10 to 40% by weight of diglycerol,
  iii. from 10 to 50% by weight of triglycerol,
  iv. from 5 to 25% by weight of tetraglycerol, and
  v. from 0 to 55% by weight of pentaglycerol and higher glycerols;
  wherein the polyglycerol has a hydroxyl number of from 1520 to 845 and wherein the carboxylic acid mixture of a), b), c) and d) make up at least 80% by weight based on the total carboxylic acid mixture, and
  wherein, in the esterification, the molar ratio of b) to c) is from 0.5:1.0 to 1.0:0.5, and further comprising homogenizing an aqueous phase, an oil phase and said polyglycerol partial ester to form the quick-break emulsion, wherein the quick-break emulsion comprises the polyglycerol partial ester, and the quick-break emulsion contains an internal aqueous phase of from 83% by weight to 94.5% by weight and an external oil phase in an amount of from 5% by weight to 17% by weight, and from 0.5% by weight to 2.0% by weight of the polyglycerol partial ester, wherein the % by weight are based on the total emulsion.

12. A cosmetic or pharmaceutical preparation comprising from 0.5% by weight to 20% by weight of the quick-break emulsion according to claim 1.

13. The cosmetic or pharmaceutical preparation according to claim 12, wherein the quick-break emulsions comprises
  an internal aqueous phase in an amount from 83% by weight to 92% by weight,
  an external oil phase in an amount from 8% by weight to 17% by weight, and
  the polyglycerol partial ester in an amount from 0.5% by weight to 2.0% by weight.

14. A pharmaceutical preparation comprising the quick-break emulsion according to claim 1.

15. The quick-break emulsion according to claim 1, wherein the quick-break emulsion contains an internal aqueous phase of from 83% by weight to 92% by weight and an external oil phase in an amount of from 8% by weight to 17% by weight, and wherein the amount of polyglycerol partial ester is from 0.5% by weight to 1.5% by weight wherein the % by weight are based on the total emulsion.

16. The quick-break emulsion according to claim 1, wherein the carboxylic acid mixture consists of:
  a) the polyhydroxycarboxylic acid of a hydroxycarboxylic acid having from 14 to 18 carbon atoms,
  b) at least one short-chain dicarboxylic acid having from 8 to 12 carbon atoms,
  c) at least one long-chain dicarboxylic acid having from 34 to 38 carbon atoms, and
  d) at least one fatty acid selected from linear, unsaturated and branched, saturated fatty acids having from 16 to 20 carbon atoms, and wherein the polyglycerol has an average degree of condensation of from 3 to 5.

17. The quick-break emulsion according to claim 1, wherein the polyhydroxycarboxylic acid has an average degree of condensation of 3 to 5.

18. The quick-break emulsion according to claim 1, wherein the short-chain dicarboxylic acid is sebacic acid.

19. The quick-break emulsion according to claim 1, wherein the degree of esterification is from 45 to 85% of all OH groups present in the polyglycerol partial ester, including the ones present in the polyhydroxycarboxylic acid.

20. The quick-break emulsion according to claim 1, wherein, in the esterification,
  from 0.4 to 8 mol of a),
  from 0.3 to 0.6 mol of b),
  from 0.2 to 0.5 mol of c), and
  from 1.2 to 2.2 mol of d)
  are used per mole of polyglycerol.

* * * * *